United States Patent [19]
Jolidon et al.

[11] Patent Number: 4,585,887
[45] Date of Patent: Apr. 29, 1986

[54] PROCESS FOR THE PRODUCTION OF OPTICALLY ACTIVE 3-AMINOCARBOXYLIC ACID ESTERS

[75] Inventors: Synèse Jolidon, Therwil; Thomas Meül, Visp, both of Switzerland

[73] Assignee: Lonza Ltd., Gampel, Switzerland

[21] Appl. No.: 677,986

[22] Filed: Dec. 4, 1984

[30] Foreign Application Priority Data

Dec. 7, 1983 [CH] Switzerland .......................... 6532/83

[51] Int. Cl.$^4$ ............................................ C07C 101/18
[52] U.S. Cl. ........................................ 560/38; 560/35; 560/155; 560/168; 560/173; 562/443; 562/553; 562/576
[58] Field of Search .......................... 560/155, 38, 173; 562/553, 443; 567/576

[56] References Cited
U.S. PATENT DOCUMENTS
2,777,873 1/1957 Hasek .................. 560/155

FOREIGN PATENT DOCUMENTS
1073501 1/1960 Fed. Rep. of Germany ...... 562/553

OTHER PUBLICATIONS
Emerson, "Organic Reactions," vol. IV, pp. 174–202, (1948).
Furukawa et al., Chem. Pharm. Bull. 27 (9), pp. 2223 to 2226, (1979).

Primary Examiner—Michael L. Shippen
Attorney, Agent, or Firm—Fisher, Christen & Sabol

[57] ABSTRACT

Process for the production of an optically active 3-aminocarboxylic acid ester from a β-keto acid ester. The β-keto acid ester is converted with a chiral amine into the corresponding enamine. The enamine is converted by hydrogenation in the presence of a platinum catalyst into the corresponding N-substituted amino acid esters. Such ester mix is converted by means of HCl gas into the hydrochlorides. The latter are neutralized. Then by liberation and isolation from the neutralized products by hydrogenolysis in the presence of a palladium catalyst, the desired optically-active 3-aminocarboxylic acid ester is obtained.

11 Claims, No Drawings

PROCESS FOR THE PRODUCTION OF OPTICALLY ACTIVE 3-AMINOCARBOXYLIC ACID ESTERS

BACKGROUND OF THE INVENTION

1. Field Of The Invention

The invention relates to a process for the production of optically active 3-aminocarboxylic acid esters from the corresponding β-keto acid esters and the corresponding acids by saponification of the esters.

2. Prior Art

The 3-aminocarboxylic acid esters are basic building compounds, which in their β-lactam form are contained in numerous antibiotics and in optically active form in naturally occurring peptides.

Optically active β-amino acids have been produced by hydrogenolysis of chiral enamines with 10 percent palladium hydroxide on coal, or with sodium cyanoboron hydride in optical purities of 3 to 28 percent and yields of 11 to 32 percent [Furukawa et al. Chem. Pharm. Bull. 27 (9) 2223 to 2226 (1979)]. In such process, the bad optical purities of such products turned out to be disadvantageous.

BROAD DESCRIPTION OF THE INVENTION

An object of the invention is to provide a process which permits the production of optically active 3-aminocarboxylic acid esters and the corresponding acids by saponification in high optical yields. Other objects and advantages of the invention are set herein or are obvious herefrom to one ordinarily skilled in the art.

The objects and advantages of the invention are achieved by the process of the invention.

The invention involves a process for converting a β-keto acid ester with a chiral amine into the corresponding enamine. On the basis of the built-in chiral auxiliary substance, the subsequent hydrogenation takes a diastereo selective course in the presence of a platinum catalyst into N-substituted amino acid esters. The separation of the diastereomeric mixture takes place by way of the corresponding hydrochlorides, producable with hydrochloric acid gas in anhydrous solvents, whereby one makes use of their variable solubility behavior to achieve separation thereof. Subsequent neutralization of the desired hydrochloride and splitting off of the N-substituent by hydrogenolysis in the presence of a palladium catalyst leads to the desired optically active 3-aminocarboxylic acid ester, which can then be converted into the corresponding optically-active 3-aminocarboxylic acid.

In this sequence of reactions, it is of decisive signifance that, for the hydrogenation of the enamine-double binding, the more selective platinum catalyst is used, which avoids a simultaneously splitting off of the chiral auxiliary group. The removal of the chiral auxiliary group succeeds with the help of the palladium catalyst, after the desired diastereomeric compound has been enriched in the hydrochlorides step.

Preferably phenylethylamine is the chiral amine. Preferably the hydrogenation of the enamine is carried out by means of hydrogen in the presence of a platinum catalyst. Also, preferably one uses 3 to 5 percent by weight of platinum catalyst, related to enamine used, which has 2 to 10 percent of platinum on a single type of carrier material in the hydrogenation step. The separation of the diastereomeric hydrochlorides of the N-substituted amino acid esters is preferably achieved by means of recrystallization. Preferably the hydrogenolysis is carried out in the presence of a palladium catalyst. Preferably one uses 9 to 15 percent by weight of palladium catalyst, related to the N-substituted aminocarboxylic acid ester, which has 2 to 10 percent of palladium on a single type of carrier material, in the hydrogenolysis step. The 3-aminocarboxylic acid ester, produced according to the invention process, is preferably converted into an acid by saponification.

DETAILED DESCRIPTION OF THE INVENTION

The β-ketonic acid esters compounds can have the formula:

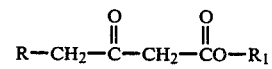

wherein R is H or straight chained or branched alkyl, which is substituted or unsubstituted, or substituted or unsubstituted benzyl, and $R_1$ is straight chained or branched alkyl, which is substituted or unsubstituted, or substituted or unsubstituted benzyl. Preferably in the formula of the β-ketonic acid ester compound, R is H, or alkyl having 1 to 4 carbon atoms, or benzyl, and $R_1$ is alkyl having 1 to 4 carbon atoms.

The conversion to the enamine is carried out advantageously with optically active 1-phenyl-ethylamine as the chiral amine. At the same time, one can proceeds in the customary manner in a solvent in the presence of an acid catalyst.

The subsequent hydrogenation of the enamine to the N-substituted amino acid ester is carried out in the presence of a platinum catalyst, which preferably has 5 percent platinum on a carrier material, such as, pumice stone, coal, silica gel or alumina. Advantageously, however, the carrier material is coal. The quantity of catalyst may be kept small. Effectively to 3 to 5 percent by weight, preferably 4 percent by weight, related to the enamine of platinum catalyst is used.

The conversion is effectively conducted at 20° to 40° C., preferably at ambient temperature.

The hydrogenation is carried out preferably at standard pressure.

According to such reduction, a diastereo mix of RR and RS or SS and SR-diastereomer results.

The subsequent conversion into the corresponding diastereomeric hydrochlorides can be carried out effectively with an excess of hydrochloric acid gas in an anhydrous solvent, such as, ether, tetrahydrofuran or dioxane. Preferably the anhydrous solvent is ether.

The separation of the diastereomeric hydrochlorides can be achieved by recrystallization in a suitable solvent or solvent mixture. The solvent or solvent mixture can be aliphatic alcohols having a $C_1$ to $C_5$-chain, such as, methanol, ethanol or butanol. In the case of methanol, the crystallization process can be initiated by the addition of ketones or carboxylic acid esters, such as, acetone or acetic ester. Mixtures of chlorinated hydrocarbons, such as, chloroform or methylene chloride, with ketones or carboxylic acid esters are suitable. The procedure can be repeated several times for the purpose of achieving a pure diastereomer. As a rule, an enrichment greater than 95 percent of a diastereomer is achieved after two times recrystallization.

The largely optically-pure hydrochloride can be neutralized in a customary manner by the addition of a suitable base, such as, aqueous ammonia solution.

Subsequently the separated N-substituted 3-aminocarboxylic acid ester is subjected to hydrogenolysis. The hydrogenolysis is conducted in the presence of a palladium catalyst which has 2 to 10 percent, preferably 5 percent of palladium, which can be on a carrier material, such as, pumice stone, coal or alumina, preferably coal, in an alcoholic solvent, such as, methanol, ethanol or propanol. The quantity of catalyst used is effectively 9 to 15 percent by weight, preferably 9 to 12 percent by weight, related to the N-substituted 3-aminocarboxylic acid ester.

The conversion is effectively conducted at 20° to 40° C., preferably at ambient temperature.

The hydrogenation pressure can be between $1 \times 10^5$ and $1 \times 10^6$ Pa, preferably standard pressure.

After the customary reprocessing by separation from the catalyst, evaporation of the solution and distillation, the optically active 3-aminocarboxylic acid ester is isolated.

For the production of the free, optically active amino carboxylic acids, the 3-aminocarboxylic acid ester is saponified in a last step. This is accomplished by heating the amino ester to a temperature of effectively 80° to 90° C., preferably 85° C., in an acid medium. Mineral acids, such as, concentrated hydrochloric acid, are used as the acid medium. The conversion time is between 3 and 6 hours. After the customary processing, for example, in the sequence of evaporating of the acid medium, absorping the residue in an alcoholic solvent, and neutralizating the hydrochloride by adding an organic amine, the free 3-aminocarboxylic acid can be preserved. The optically active 3-aminocarboxylic acids produced in this manner, are present in an optical purity of greater than 90 percent.

The process of the invention is demonstrated in Example 1 below on the basis of the production of R-(−)-3-aminobutyric acid. Acetoacetic acid methyl ester is converted with R-(+)-1-phenylethylamine and acetic acid in toluene. After the customary finishing by evaporation of the solvent and high vacuum distillation, the corresponding enamine is obtained. This is subsequently hydrogenated, as described, effectively in methanol as the solvent. After processing by evaporation of the solvent and high vacuum distillation, the corresponding 3-(1'-methylbenzylamino)-butyric acid methyl ester is obtained as a diastereomer mixture, whereby an enrichment of RR-isomer has occurred. For the subsequent hydrochloride formation the diastereo mixture is dissolved preferably in ether and it is subsequently saturated with hydrogenchloride. After the filtration and drying of the precipitated crystal paste, the pure hydrochloride can again be obtained as a diastereomer mixture. For the separation of the diastereomer mixture, the hydrochlorides are recrystallized hot from methanol-/acetone. After recrystallization twice, there is an enrichment of the RR-isomer of at least 95 percent. The largely pure diastereomer can be neutralized in a first step by the addition of aqueous ammoniac solution for achieving of the enantiomer end product. The free amine can then, after effective isolation by extraction or distillation for the splitting off of the methyl benzyl substituents, be subjected to hydrogenolysis in the presence of a palladium catalyst. The subsequent distillation produces the R-(−)-3-aminobutyric acid methyl ester, which can be saponified into the R-(−)-3-aminobutyric acid. The optical purity of the R-(−)-3-aminobutyric acid thusly-produced in greater than 90 percent.

The same synthesis can also be carried out with S-(−)-1-phenylethylamine. The S-(+)-3-aminobutyric acid methyl ester or the S-(+)-3-aminobutyric acid in the same optical purity is obtained.

Examples 2 to 4 below show the process of the invention for the production of the aminopentane-, aminohexane and aminobenzylbutyric acid esters.

By way of summary, optically-active 3-aminocarboxylic acid ester, as well as the free, optically-active 3-aminocarboxylic acids, are produced starting out from β-ketone acid esters and chiral amines by way of diastereomer separation of N-substituted amino acid ester hydrochlorides.

As used herein, all parts, percentages, ratios and proportions are on a weight basis, unless otherwise stated herein or otherwise obvious herefrom to one ordinarily skilled in the art.

EXAMPLE 1

Production Of Optically Pure 3-Aminobutyric Acids 1.1 Production Of 3-(1'-methylbenzylamino)-2Z-butenic Acid Esters (a) A mixture of 54.6 g (0.47 mole) of acetoacetic acid methyl ester, 54.5 g (0.45 mole) of R-(+)-1-phenylethylamine and 1.0 g of acetic acid was kept in 150 ml of toluene for 2 hours at reflux. The reaction water (8.3 ml; 102 percent of theory) was removed by means of a water separator. Subsequently, the solution was evaporated in the rotatory evaporator and was distilled under high vacuum. At the same time, as a main fraction (boiling point $_{0.4}$ of 108° C.), 84.6 g (86 percent of R-(−)-(1'-methylbenzylamino)-2Z-butenic acid ester was isolated as a colorless oil, $[\alpha]_D 25$ (c=2; EtOH) = −545°.

UV (in EtOH): $\lambda_{max.} = 287$ nm

IR (film): 3280 (NH), 1655 (COOCH$_3$), 1605/1492 (Ar), 1270 (O—CH$_3$), 760/700 (5 adjacent aromatic H's)

NMR (CDCl$_3$) : 1.50 (d; J=7 Hz; CH$_3$—CH; 3H); 1.76 (s; CH$_3$—C═; 3H); 3.64 (s; OCH$_3$; 3H); 4.47 (s; CH—; 1H); 4.62 (qaxd; J=7 Hz; Ph-CH; 1H); 7.26 (s; aromatic; 5H); 8.90 (s wide; NH; 1H).

(b) Analogously from acetoacetic acid methyl ester and S-(−)-1-phenylethylamine, the corresponding S-(+)-3-1(1'-methylbenzylamino)-2Z-butenic acid methyl ester was produced. The yield was 51 percent, the boiling point $_{0.8}$ was 130° C. (partial polymerization during the distillation); and $[\alpha]_D 25$ (c=2; EtOH) was +512° C.

(c) From acetoacetic acid ethyl ester and R-(+)-1-phenylethylamine, R-(−)-3-(1'-methylbenzylamino)-2Z-butenoic acid ethyl ester was produced. The yield was 40 percent; the boiling point$_{0.6}$ was 120° C. (partial polymerization during the distillation); and $[\alpha]_D^{25}$ (c=2; EtOH) was −447° C.

UV (in EtOH): $\lambda_{max.} = 288$ nm

IR (film): 3280 (NH); 1650 (COOCH$_3$); 1610/1492 (Ar); 1265 (OCH$_3$); 760/700 (5 adjacent aromatic H's);

NMR (CDCl$_3$): 1.26 (t; J=7.5 Hz); (CH$_3$—CH$_2$—; 3H); 1.49 (d; J=7 Hz; CH$_3$—CH—; 3H); 1.74 (s; CH$_3$—C═; 3H); 4.08 (qa; J=7.5 Hz; CH$_2$—CH$_3$; 2H); 4.44 (s; —CH═; 1H); 4.58 (qaxd; Ph-CH; 1H); 7.20 (s; aromatic; 5H); 8.85 (s wide; NH; 1H).

(d) The R-(−)-3-(1'-methylbenzylamino)-2Z-butenoic acid t-butyl ester was produced from acetoacetic acid t-butylester and R-(+)-1-phenylethylamine.

The yield was 79 percent; the boiling point$_{0.4}$ was 115° C.; and $[\alpha]_D^{25}$ (c=2; EtOH) was −528° C.

IR (film): 3280 (NH); 1650 (COOCH$_3$); 1610/1490 (aromatic) 750/700 (5 adjacent aromatic H's)

NMR (CDCl$_3$): 1.47 (s; t-Bu; 9H); 1.49 (d; J=7 Hz; CH$_3$—CH; 3H); 1.71 (s; CH$^3$—C=; 3H); 4.37 (s; CH—; 1H); 4.55 (qaxd; Ph-CH—; 1H); 7.19 (s; aromatic; 5H); 8.60 (s wide; NH; 1H).

1.2 Production Of 3-(1′methylbenzylamino)-butyric Acid Esters (a) 25.0 g of R-(−)-methyl ester (0.114 mole) was dissolved in 100 ml of methanol, the solution mixed with 1.0 g platinum, (5 percent) on coal and the material was hydrogenated at ambient temperature and standard pressure. The absorption of hydrogen was completed after 10 hours and amounted to 96 percent of theory. The catalyst was filtered off, the solution was evaporated in a rotatory evaporator and the residue was distilled under high vacuum. At the same, time 23.2 g of (92 percent) of 3-(1′-methylbenzylamino)-butyric acid methyl ester was isolated as the main fraction having a boiling point$_{0.5}$ of 88° to 92° C. as a diastereomer mixture (according to NMR : 73 percent 1′R, 3R and 27 percent 1′R, 3S-isomer).

IR (film): 3430/3360 (NH); 1738 (COOCH$_3$); 1600 (aromatic); 761/702 (5 adjacent aromatic H's)

NMR (CDCl$_3$): 1.02 (d; J=6 Hz; CH$_3$—CH—CH$_2$; 3H); 1.31 (d; J=7 Hz; Ph—CH—CH$_3$; 3H); 1.53 (s wide; NH; 1H); 2.30 (d; J=5 Hz; —CH$_2$—of RS-isomer; 0.54 H); 2.42 (d; J=5 Hz; —CH$_2$ of RR-isomer; 1.46 H); 2.95 (qaxdxd; CH$_3$—CH—CH$_2$; 1H); 3.60 (s; OCH$_3$ of RS-isomer; 0.81 H); 3.63 (s; OCH$_3$ of RR-isomer; 2.19 H); 3.87 (qaxd; Ph—CH—; 1H); 7.28 (s; aromatic; 5H).

(b) Analogously from the S-(+)-methyl ester, the corresponding 3-(1′-methylbenzylamino)-butyric acid methyl ester was obtained as a diastereomer mixture (according to NMR; 73 percent of 1′S, 3S and 27 percent of 1′S, 3R-isomer). The yield was 79 percent.

(c) Starting out from R-(−)-ethyl ester, 3-(1′-methylbenzylamino)-butyric acid ethyl ester was obtained as a diasteromer mixture (according to NMR; about 65 percent 1′R, 3R and about 35 percent of 1′R, 3S-isomer). The yield was 76 percent and the boiling point$_{0.5}$ was 100° to 110° C.

IR (film) 3430/3330 (NH); 1732 (COOCH$_3$); 1600 (aromatic); 760/700 (5 adjacent aromatic. H's)

NMR (CDDl$_3$): 1.03 (d; J=7 Hz; CH$_3$—CH—2; 3H); 1.11 (t; J=7 Hz; CH$_3$—2; 3H); 1.31 (d; J=6.5 Hz; Ph-CH—CH$_3$; 3H); 1.60 (s wide; 1H); 2.28 (d; J=5 Hz; —CH$_2$—COO— of RS-isomer; 0.7 H); 2.40 (d; J=5 Hz; —CH$_2$—COO— of RR-isomer; 1.3 H); 2.95 (qaxdxd; CH$_3$—CH—CH$_2$; 1H); 3.92 (qaxdxd; Ph-CH; 1H); 4.11 (qa; —CH$_2$—CH$_3$; 2H); 7.25 (s; aromatic; 5H).

(d) From the R-(−)-t-butyl ester, 3-(1′-methylbenzylamino)-butyric acid-t-butyl ester was obtained as a diastereomer mixture (according to NMR: 73 percent of 1′R, 3R and 27 percent of 1′R, 3S-isomer). The yield was 93 percent, and the boiling point$_{0.5}$ was 95° to 97° C.

IR (film): 3430/3240 (NH); 1730 (COOCH$_3$); 1600 (aromatic); 760/700 (5 adjacent aromatic H's)

NMR (CDCl$_3$): 1.02 (d; J=7 Hz; CH$_3$—CH—CH$_2$; 3H); 1.31 (d; J=6.6 Hz; Ph-CH—CH$_3$; 3H); 1.44 (s; t-BU of the RS-isomers; 2.43 H); 1.45 (s; t-Bu of the RR-isomers; 6.57 H); 2.11 (d; J=5 Hz; —CH$_2$—of the RS-isomers; 0.54 H); 2.28 (d; J=5 Hz; —CH$_2$ of the RR-isomers; 1.46 H); 2.90 (qaxdxd; CH$_3$—CH—CH$_2$; 1H); 3.86 (qa; CH$_3$—CH-Ph; 1H); 7.23 (s; aromatic 5H).

1.3 Production And Recrystallization Of The Hydrochloride of 3-(1′-methylbenzylamino)-butyric Acid Esters (a) 20.0 g (90.4 mmoles) of the crude diastereomer mixture (73 percent of RR and 27 percent RS) of the methyl ester was put into 300 ml of ether, and the solution was saturated under cooling with gaseous hydrogenchloride. The crystal paste was drained off and dried. Finally 23.3 g (100 percent) of the hydrochloride of 3-(1′-methylbenzylamino)-butyric acid methyl ester, as the diastero mixture (melting point was 195° to 198° C.), was isolated. 16.02 g (62.1 m moles) of the hydrochloride was dissolved hot in 32 ml of methanol. By the slow addition of 80 ml of acetone, the enriched RR-isomer was brought to crystallization. Draining off and drying produced 8.55 g (53 percent) of colorless crystals of the RR-hydrochloride (melting point was 210° to 212° C.). Repeated recrystallization according to the same process finally produced an RR-hydrochloride having a melting point of 225° to 227° C.

1.4 Production Of 3-aminobutyric Acid Esters (a) 8.35 g (32.4 mmoles) of the twice recrystallized hydrochloride of the RR-methyl ester was put into 50 ml of water, was set in an alkaline manner with ammoniac solution and extracted four times with methylene chloride. The organic phases were dried over sodium sulfate, evaporated and the residue was absorbed in 70 ml of methanol. Subsequently it was treated with 0.8 g of palladium (5 percent) on coal and was hydrogenated at ambient temperature and standard pressure. The hydrogen absorption was completed after 24 hours and amounted to 95 percent of theory. The catalyst was filtered off, the resultant solution was evaporated and the residue was distilled. At the same time colorless R-(−)-3-aminobutyric acid methyl ester (boiling point$_{10}$ was 60° C.) was isolated as the main fraction 2.78 g (73 percent). $[\alpha]_D^{25}$ (c=1; EtOH) was −32.0°.

IR (film); 3380/3300 (NH$_2$); 1735 (COOCH$_3$); 1595 (NH$_2$)

NMR (CDCl$_3$): 1.13 (d; J=6.5 Hz; CH$_3$—CH; 3H); 1.49 (s; NH$_2$; 2H); 2.0-2.7 (m; —CH$_2$; 2H); 3.37 (sex. with fine splitting off, J about 6.5 Hz; —CH—; 1H); 3.67 (s; OCH$_3$; 3H).

(b) Analogously from the twice recrystallized hydrochloride of the SS-methyl ester, the corresponding S-(+)-3-aminobutyric acid methyl lester was obtained at a 73 percent yield.

$[\alpha]_D^{25}$ (c=1; EtOH)= +32.3° .

1.5 Production of 3-aminobutyric Acids (a) 700 mg (5.98 mmoles) of the R-(−)-methyl ester was put into 8 ml of concentrated hydrochloric acid and was kept there for 5 hours at 85° C. The reaction mixture was evaporated, was dissolved in 2 ml of methanol and was mixed slowly with 1.11 g (5.98 mmoles) of tributylamine. The precipitation was completed by the addition of 15 ml of methylene chloride. Draining off and drying of the solid body finally produced 550 mg (89 percent) of colorless R-(−)-3-aminobutyric acid. The melting point thereof was 214° to 215° C. $[\alpha]_D^{25}$ (c=1; H$_2$O) was −34.8° (optical purity 90 percent).

(b) Analogously from the S-(+)-methyl ester, the corresponding S-(+)-3-aminobutyric acid was obtained. The yield was 80 percent; the melting point was 215° C.; and $[\alpha]_D^{25}$ (c=1; H$_2$O) was −36.5 (optical purity 94 percent).

EXAMPLE 2

Production Of The R-(−)-3-aminopentane Acid Methyl Ester

2.1 Production Of 3-(1′-methylbenzylamino)-2Z-pentene Acid Methyl Ester 62.4 g (0.47 mole) of 3-oxopentane acid methyl ester and 54.5 g (0.45 mole) of R-(+)-1-phenylethylamine were heated at reflux with 1.0 g of acetic acid in 150 ml of toluene for 3 hours. The reaction water (the 8.1 ml was 100 percent of theory) was removed by means of a water separator. The solution was then reduced on the rotation evaporator and finally distilled under high vacuum. 94.2 g of product having a purity of 99.6 percent was isolated as the main fraction (boiling point $_{0.07}$ was 118° C.).

UV (in MeOH) $\lambda_{max.}$=289 nm ($\epsilon_{max.}$=10010)
IR (thin layer) [cm$^{-1}$]: 3280 (NH), 1660 (CO, ester) 1660 (aromatic, C=C)
NMR (CDCl$_3$) 300 Mhz : 1.0 (t; J=7.5 Hz; 3CH$_3$); 1.52 (d; J=6.8 Hz; 3CH$_3$); 1.99 (—CH$_2$—); 2.16 (—CH$_2$); 3.67 (s; esterprot); 4.52 (s; olefinprot); 4.67 (methinprot); 7.35–7.2 (aromatic. H); 9.03 (d, wide, 1NH-prot).

2.2 Production Of 3-(1′-methylbenzylamino)-pentene Acid Methyl Ester 25.0 g (0.102 mole) of 3-(1′-methylbenzylamino)-2Z-pentene acid methyl ester was dissolved in 100 ml of absolute methanol; the solution was mixed with 1.0 g of platinum (5 percent) on coal, and hydrogenated at ambient temperature and standard pressure. After 24 hours the hydrogen absorption was complete (2.9 1). It was filtered off from the catalyst, the reaction solution was concentrated and the residue was distilled under high vacuum. 21.3 g of product having a purity of 99.2 percent was obtained as the main fraction (boiling point $_{0.3}$ was 75° C.).

IR (thin layer) [cm$^{-1}$]: 3340 (NH); 1730 (CO, ester); 1600 (aromatic C=C)
NMR (CDCl$_3$) 300 Mhz : 0.85 (t; J=7.4 Hz; 3CH$_3$ prot); 1.31 (d; J=6.6 Hz; 3CH$_3$ prot); 1.40 (2—CH$_2$—prot); 1.48 (s; wide; 1 NH-prot); 2.32 (2CH$_3$ of the RS isomer); 2.43 (2—CH$_2$—of the RR isomer); 2.72 (1 methinyprot); 3.61 (s; 3 esterprot of the RS isomer); 3.66 (s; 3 esterprot of the RR isomer); 3.87 (q; 1 methinprot; J=6.5 Hz); 7.4–7.18 (5 aromatic prot).

2.3 Production And Recrystallization Of The Hydrochloride Of The 3-(1′-methylbenzylamino)-pentane Acid Methyl Ester 28.6 of the crude diastereomer mixture of methyl ester was dissolved in 410 ml of ether and the solution, while being cooled with ice, was saturated with gaseous hydrogenchloride. The crystal paste was drawn off and dried. 31.0 g of hydrochloride of the 3-(1′-methylbenzylamino)-pentane acid methyl ester was isolated as diasteromer mixture having a melting point of 174 to 174° C. 31.0 g of the crude hydrochloride was dissolved hot in 50 ml of methanol and was brought to precipitation by the addition of 160 ml of acetone. 9.9 g of a white product having a melting point of 195° to 196° C. was obtained.

2.4 Production Of The R-(−)-3-aminopentane Acid Ester 9.8 g (0.036 mole) of the recrystallized hydrochloride of the RR-methyl ester was dissolved in 50 ml of water set with ammoniac solution in an alkaline manner and was extracted four times, always with 50 ml of methylene chloride. The organic phases were dried over sodium sulfate,, were evaporated and the residue was absorbed in 120 ml of methanol. Subsequently, the residue was treated with 1.2 g of palladium (5 percent) on coal and hydrogenated at ambient temperature and standard pressure. The hydrogen absorption was completed after 38 hours. The catalyst was filtered off, the solution was evaporated and the residue was distilled. At the same time 3.6 g of product having a content of 88.9 percent was isolated as the main fraction (boiling point$_4$ was 52° to 57° C.). The optical rotation of the fraction was $[\alpha]_D^{25}$=−26.1° (c=1, EtOH).

IR [cm$^{-1}$]: 3385; 3300 (NH); 1733 (CO, ester); 1595 (NH); 840 (NH wagging)
NMR (CDCl$_3$) 300 Mhz: 0.94 (t; J=7.2 Hz; 3CH$_3$ prot); 1.43 (2-CH$_2$—prot); 1.45 (s, wide; 2NH-prot); 2.26 (1—CH$_2$—prot; J=9 Hz); 2.48 (1—CH$_2$—prot); 3.11 (1-methinprot); 3.69 (s; 3 esterprot).

EXAMPLE 3

Production Of R-(−)-3-aminohexane Acid Ethyl Ester

3.1 Production Of The 3-(1′-methylbenzylamino)2Z-hexene Acid Ethyl Ester 76.6 g (0.47 mole) of butyryl acetic acid ethyl ester, 54.5 g (0.45 mole) of R-(+)-1-phenylethylamine and 1.0 g of concentrated acetic acid were dissolved in 150 ml of toluene and were heated at reflux for 3 hours. The reaction water (8.5 ml) was removed by means of a water separator. Subsequently, the solution was concentrated on the rotation evaporator. 125.6 g of colorless solution (raw product) remained as residue. 125.6 g of the raw product was distilled under the high vacuum. As the main fraction (boiling point$_{0.08}$ was 147° C.), 108.3 g of product was obtained which had a purity of 99.3 percent.

UV (in EtOH): $\lambda_{max.}$=288 nm ($\epsilon_{max.}$=21212) 205 nm ($\lambda_{max.}$=10808)
IR (thin layer) [cm$^{-1}$]: 3280 (NH); 1650 (CO ester); 1600 (aromatic, C=C); 760, 700 (C—H aromatic)
NMR (CDCl$_3$) 300 Mhz : 0.87 (t, 3CH$_3$ prot; J=7.5 Hz); 1.27 (t; 3 esterprot; J=8.0 Hz); 1.33–1.55 (3-CH$_3$ prot; J=7.0 Hz); 1.51 (d; 3CH$_3$ prot; J=6.8 Hz); 1.86–2.16 (2-CH$_2$-prot); 4.13 (q; 2 esterprot); 4.50 (s; 1-olefinprot); 4.64 (q; 1 methinprot); 7.18–7.35 (5 aromatic prot); 9.03 (d; wide, 1 NH prot).

3.2 Production Of The 3-(1′-methylbenzylamino)-hexane Acid Ethyl Ester 52.2 g (0.1 mole) of 3-(1′-methylbenzylamino)-2Z-hexene acid ethyl ester was dissolved in 200 ml of absolute ethanol, with 2.0 g of platinum (5 percent) on coal and was hydrogenated at ambient temperature and standard pressure. After 27 hours the hydrogen absorption was completed (4.25l). The solution was filtered from the catalyst, the reaction solution was evaporated and the residue was distilled under high vacuum. Obtained was:

1st fraction, 0.6 g, GC: 81.2%, boiling point$_{0.05}$=82° C.

2nd fraction, 5.7 g, GC: 86.5%, boiling point$_{0.05}$ = 95° C.

3rd fraction, 37.7 g, GC: 97.4%, boiling point$_{0.04}$ = 105° C.

4th fraction, 3.9 g, GC: 57.7%, boiling point$_{0.08}$ = 116° C.

This corresponded to 44.4 g of 100 percent product, which was a 84.3 percent yield, related to 100 percent product.

UV (in EtOH) $\lambda_{max.}$ = 289 nm ($\epsilon_{max.}$ = 1106)

IR (thin layer) [cm$^{-1}$]: 3320 (NH); 1730 (CO ester); 1600 (C=C, aromatic); 760, 700 (C-H aromatic);

NMR (CDCl$_3$) 300 Mhz: 0.82 (t; 3CH$_3$ of RR isomer); 0.88 (t; 3CH$_3$ of RS isomer); 1.27 (t; 3 esterprot); 1.20–1.52 (4-CH$_2$-prot); 1.32 (d; 3CH$_3$ prot); 1.50 (s, wide; 1 NH prot); 2.27–2.50 (2-CH$_2$-prot); 2.77 (1 methinprot); 3.88 (q; 1 methinprot); 4.13 (q; 2 esterprot); 71.8–1.26 (5 aromatic prot).

3.3 Production And Recrystallization Of The 3-(1'-methylbenzylamino)-hexane Acid Ethyl Ester 36.4 g of the crude diastereomer mixture of the ethyl ester wase dissolved in 460 ml of ether and the solution was saturated with gaseous hydrogenchloride while cooling it under ice. The crystal paste was subjected to suction and dried. 29.7 g of the hydrochloride of the 3-(1'-methylbenzylamino)-hexane acid ethyl ester was isolated as diastereomer mixture having a melting point of 126° to 130° C. 28.6 g of the crude hydrochloride was recrystallized hot from 25 ml of ethanol. 15.0 g of product having a melting point of 138° to 139° C. was obtained. 15.0 g of the recrystallized hydrochloride was recrystallized once again hot from 15 ml of ethanol. 12.6 g of a white product having a melting point of 141° to 142° C. was obtained.

3.4 Production Of The R-(−)-3-amino Hexane Acid Ethyl Ester 12.5 g of the twice-recrystallized hydrochloride of the RR-ethyl ester was dissolved in 75 ml of water, was adjusted with ammoniac solution in an alkaline manner and was extracted four times, always with 50 ml of methylene chloride. The organic phases were dried by means of sodium sulfate, were evaporated and the residue was absorbed in 140 ml of ethanol. Subsequently, the residue was mixed with 1.4 g of palladium (5 percent) on coal and was hydrogenated at ambient temperature and at standard pressure. The hydrogen absorption was completed after 38 hours. The catalyst was filtered off, the solution was evaporated and the residue was distilled. At the same time the following was isolated:

1st fraction, 1.01 g, GC: 88.7%, boiling point$_2$ = 55° C.

2nd fraction, 3.62 g, GC: 95.5%, boiling point$_2$ = 57° C.

3rd fraction, 0.30 g, GC: 96.6%, boiling point$_2$ = 56° C.

This corresponded to 4.65 g of 100 percent product, which was a 70.0 percent yield. The optical rotation of the 2nd fraction was $[\alpha]_D^{25}$ = −23.2° . (c=1, EtOH).

IR [cm$^{-1}$]: 3380, 3300 (NH—); 1734 (CO, ester); 1595 (NH); 840 (NH wagging);

NMR (CDCl$_3$) 300 Mhz: 0.94 (3—CH$_3$ prot); 1.27 (t; 3 ester prot); 1.30–1.50 (4-CH$_2$ prot); 1.43 (s, wide; 2NH prot); 2.24 (1—CH$_2$-prot); 2.46 (1—CH$_2$-prot); 3.13–3.24 (1 methyinprot); 4.16 (q; 2 esterprot; J=7.1 Hz).

EXAMPLE 4

Production Of R-(−)-3-amino-4-benzyl butyric Acid Methyl Ester

4.1 Production Of The 3-(1'-methylbenzylamino)-4-benzyl-2Z-butenoic Acid Methyl Ester 40.5 g (0.2 mole) of 3-oxo-4-benzylbutyric methyl ester, 24.2 g (0.2 mole) of R-(+)-1-phenylethylamine and 1.0 g of concentrated acetic acid were dissolved in 100 ml of toluene and were heated at reflux for 1.5 hours. The reaction water (3.6 ml) was removed by means of a water separator. Subsequently, the solution was concentrated on the rotation evaporator. The residue was filtered with ether/petroleum ether by means of silica gel at 1:1. 66.85 g of raw product (GC was 89.2 percent) was obtained. This corresponded to 59.6 g of 100 percent product, which was a 96.3 percent yield, related to 100 percent R-(+)-1-phenyl ethyl amine.

UV (in EtOH): $\lambda_{max.}$ = 289 nm ($\epsilon_{max.}$ = 18914) 205 nm ($\epsilon_{max.}$ = 13339)

IR (thin layer) [cm$^{-1}$]: 3280 (NH); 1655 (CO, ester); 1605 (C=C, aromatic) 790, 700 (C—H, aromatic)

NMR (CDCl$_3$) 300 Mhz: 1.47 (d; 3—CH$_3$ prot); 2.19–2.44 (2—CH$_2$ prot); 2.52–2.78 (2—CH$_2$ prot); 3.67 (s; 3 esterprot); 4.55 (q; 1 methinprot); 4.58 (s; 1 olefinprot); 6.97–7.34 (10 aromatic prot); 9.06 (d, wide; 1NH prot).

4.2 Production Of The 3-(1'-methylbenzylamino)-4-benzylbutenoic Acid Methyl Ester 15.3 g (0.49 mole) of 3-(1'-methylbenzylamino)-4-benzyl-2Z-butyric acid methyl ester was dissolved in 50 ml of absolute methanol, was mixed with 0.5 g of platinum (5 percent) on coal and was hydrated at ambient temperature and standard pressure. After 60 hours in the hydrogen absorption was completed (1.2 l). It was filtered off from the catalyst, the reaction solution was evaporated and the residue was distilled in the high vacuum. 13.8 g of product (GC was 93.2 percent, boiling point$_{0.3}$ was 156° C.) was obtained. This corresponded to 12.9 g of a 100 percent product, which was a 83.8 percent yield.

NMR (CDCl$_3$) 300 Mhz: 1.38 (d; 3HC$_3$ prot of RS isomer); 1.41 (d; 3CH$_3$ prot of RR isomer); 1.70 (s; wide; 1 NH prot); 1.70–1.95 (2—CH$_2$-prot); 2.44–3.00 (4—CH$_2$-; 1 methinprot); 3.62 (s; 3 esterprot of RS isomer); 3.65 (s; 3 esterprot of RR isomer); 3.87 (quintet, 1 methinprot); 7.01–73.8 (10 aromatic prot).

4.3 Production And Recrystllaization Of The Hydrochloride Of The 3-(1'-methylbenzylamino)-4-benzylbutyric Acid Methyl Ester 13.8 g of the raw diastereomer mixture of the methyl ester was dissolved in 150 ml of ether and the solution was saturated with gaseous hydrogenchloride while being cooled with ice. The crystal paste was subjected to suction and dried. 12.3 g of the hydrochloride was isolated as diastereomer mixture having a melting point of 177° to 180° C. 12.2 g of this product was dissolved hot in 27 ml of methanol and was made to precipitate by the addition of 75 ml of acetone. 6.3 g of product having a melting point of 189° to 190° C., was obtained.

4.4 Production Of The R-(−)-3-amino-4-benzyl butyric Acid Methyl Ester 6.2 g of the recrystallized hydrochloride of the RR-methyl ester was dissolved in 50 ml of water, was adjusted in an alkaline manner with ammoniac solution and was extracted four times, always with 50 ml of methylene chloride. The organic phases were dried over sodium sulfate, were evaporated and the residue was absorbed in 60 ml of absolute methanol. Subsequently, the residue solution was mixed with 0.6 g of palladium (5 percent) on coal and was hydrogenated at ambient temperature and standard pressure. The hydrogen absorption was completed after 60 hours. The catalyst was filtered off, the solution was evaporated and the residue was distilled.

1st fraction, 0.9 g, GC: 93.5%, boiling point$_{0.2}$: 98° C.
2nd fraction, 1.4 g, GC: 95.4%, boiling point$_{0.2}$: 100° C.
3rd fraction, 0.1 g, GC: 93.7%, boiling point$_{0.1}$: 95° C.
This corresponds to a yield of 2.3 g of 100 percent product, which was a 60.8 percent yield. The optical rotation of the 2nd fraction was $[\alpha]_D^{25}$ −2.3° (c=1, EtOH).

UV (in EtOH): $\lambda_{max.}=208$ nm ($\epsilon_{max.}=8414$)
IR (thin layer) [cm$^{-1}$]: 3390 (NH); 1735 (C) ester); 1600 (C=C aromatic); 1590 (NH); 750, 700 (C—H aromatic);
NMR (CDCl$_3$) 300 Mhz: 1.45 (s; wide; 2NH prot); 1.58–1.82 (2—CH$_2$-prot); 2.31 (1—CH$_2$-prot); 2.50 (1—CH$_2$-prot); 2.58–2.80 (2-CH$_2$-prot). 3.21 (1-methyinprot); 3.68 (s; 3 esterprot); 7.14–7.33 (5 aromatic prot).

What is claimed is:

1. Process for the production of an optically-active 3-aminocarboxylic acid ester from a β-keto acid ester, the β-ketonic acid esters compounds having the formula:

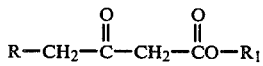

wherein R is H, a straight chained alkyl, which is substituted or unsubstituted, a branched alkyl, which is substituted or unsubstituted, or substituted or unsubstituted benzyl, and R$_1$ is a straight chained alkyl, which is substituted or unsubstituted, a branched alkyl, which is substituted or unsubstituted, or substituted or unsubstituted benzyl, comprising:
   (a) converting the β-keto acid ester with a chiral amine into the corresponding enamine;
   (b) converting the corresponding enamine by hydrogenation in the presence of a platinum catalyst into a mixture of corresponding N-substituted amino acid esters;
   (c) converting the mixture of corresponding N-substituted amino acid esters by introducing HCl gas into a mixture of corresponding hydrochlorides;
   (d) neutralizing the mixture of corresponding hydrochlorides; and
   (e) liberating and isolating from the mixture of neutralized products by hydrogenolysis, in the presence of a palladium catalyst, the desired optically-active 3-amino-carboxylic acid ester.

2. Process as claimed in claim 1 wherein, in the formula of the β-ketonic acid ester compound, R is H, an alkyl having 1 to 4 carbon atoms or benzyl, and R$_1$ is an alkyl having 1 to 4 carbon atoms.

3. Process as claimed in claim 1 wherein the chiral amine is 1-phenylethylamine.

4. Process as claimed in claim 3 wherein 3 to 5 percent by weight of platinum catalyst, related to enamine used, which has 2 to 10 percent of platinum on one carrier material, is used in the hydration step.

5. Process as claimed in claim 3 wherein the separation of the diastereomeric hydrochlorides of the N-substituted amino acid esters is achieved by means of recrystallization.

6. Process as claimed in claim 3 wherein 9 to 15 percent by weight of palladium catalyst, related to the N-substituted amino carboxylic acid ester, which has 2 to 10 percent of palladium on a carrier material, is used in the hydrogenolysis step.

7. Process as claimed in claim 1 wherein 3 to 5 percent by weight of platinum catalyst, related to enamine used, which has 2 to 10 percent platinum on a carrier material, is used in the hydrogenation step.

8. Process as claimed in claim 1 wherein one carries out the separation of the diastereomeric hydrochlorides of the N-substituted amino acid esters is achieved by means of recrystallization.

9. Process as claimed in claim 1 wherein 9 to 15 percent by weight of palladium catalyst, related to the N-substituted amino carboxylic acid ester, which has 2 to 10 percent of palladium on a carrier material, is used in the hydrogenolysis step.

10. Process for the production of an optically-active 3-aminocarboxylic acid from a β-keto acid ester, the β-ketonic acid esters compounds having the formula:

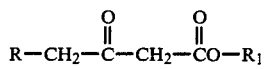

wherein R is H, a straight chained alkyl, which is substituted or unsubstituted, a branched alkyl, which is substituted or unsubstituted, or substituted or unsubstituted benzyl, and R$_1$ is a straight chained alkyl, which is substituted or unsubstituted, a branched alkyl, which is substituted or unsubstituted, or substituted or unsubstituted benzyl, comprising:
   (a) converting the β-keto acid ester with a chiral amine into the corresponding enamine;
   (b) converting the corresponding enamine by hydrogenation in the presence of a platinum catalyst into a mixture of corresponding N-substituted amino acid esters;
   (c) converting the mixture of corresponding N-substituted amino acid esters by introducing HCl gas into a mixture of corresponding hydrochlorides;
   (d) neutralizing the mixture of corresponding hydrochlorides; and
   (e) liberating and isolating from the mixture of neutralized products by hydrogenolysis, in the presence of a palladium catalyst, the optically-active 3-amino-carboxylic acid ester; and
   (f) converting the optically-active 3-aminocarboxylic acid ester by means of saponification into the optically-active 3-aminocarboxylic acid.

11. Process as claimed in claim 10 wherein the saponification is achieved by means of a mineral acid.

* * * * *